United States Patent
Fuchs et al.

(10) Patent No.: US 8,609,419 B2
(45) Date of Patent: Dec. 17, 2013

(54) METHOD FOR INSERTING A NUCLEIC ACID OF INTEREST INTO A PROKARYOTIC OR EUKARYOTIC CELL BY HOMOLOGOUS RECOMBINATION

(75) Inventors: Robert Fuchs, Strasbourg (FR); Marc Bichara, Vendenheim (FR)

(73) Assignee: Centre National de la Recherche Scientifique, Paris (FR)

( * ) Notice: Subject to any disclaimer, the term of this patent is extended or adjusted under 35 U.S.C. 154(b) by 1218 days.

(21) Appl. No.: 10/532,663

(22) PCT Filed: Oct. 27, 2003

(86) PCT No.: PCT/FR03/03188
§ 371 (c)(1),
(2), (4) Date: Dec. 5, 2005

(87) PCT Pub. No.: WO2004/039983
PCT Pub. Date: May 13, 2004

(65) Prior Publication Data
US 2006/0270039 A1    Nov. 30, 2006

(30) Foreign Application Priority Data

Oct. 28, 2002 (FR) ...................................... 02 13474

(51) Int. Cl.
*C12N 15/01*    (2006.01)

(52) U.S. Cl.
USPC ............ 435/441; 435/448; 435/462; 435/477

(58) Field of Classification Search
None
See application file for complete search history.

(56) References Cited

U.S. PATENT DOCUMENTS

2003/0124605 A1 *    7/2003    Hoeijmakers et al. ............ 435/6

FOREIGN PATENT DOCUMENTS

WO    WO 01/68882 A    9/2001

OTHER PUBLICATIONS

Ganiatsas et al "SEK1 deficiency reveals mitogen-activated protein kinase cascade crossregulation and leads to abnormal hepatogenesis" Proc. Natl. Acad. Sci. USA vol. 95, pp. 6881-6886, Jun. 1998.*
Hinds et al in "Enhanced gene replacement in mycobacteria" [Microbiology, 1999, vol. 145: p. 519-527.*
Hinds J et al: "Enhanced gene replacement in mycobacteria.", Microbiology (Reading, England) England Mar. 1999, vol. 145 (Pt 3), Mar. 1999, pp. 519-527, XP002246130, ISSN: 1350-0872, the whole document.
Maher V M et al:, "Mutations and Homologous Recombination Induced by N-Substituted Aryl Compounds in Mammalian Cells", Environmental Science Research 1990, pp. 149-156, XP008018516, ISSN: 0090-0427, the whole document.
Posfai G et al:, "Markerless gene replacement in *Escherichia coli* stimulated by a double-strand break in the chromosome", Nucleic Acids Research, Oxford University Press, Surrey, GB, vol. 27, No. 22, Nov. 15, 1999, pp. 4409-4415, XP002963851, ISSN: 0305-1048.
Nairn R S et al:, "Transformation depending on intermolecular homologous recombination is stimulated by UV damage in transfected DNA" Mutation Research 1988 Netherlands, vol. 208, No. 3-4, 1988, pp. 137-141, XP002281444, ISSN: 0165-7992.
Dianov G L et al:, "The Chemical Mutagen Dimethyl Sulfate Induced Homologous Recombination of Plasmid DNA by Increasing the Binding of RECA Protein to Duplex DNA" Mutation Research, vol. 249, No. 1, 1991, pp. 189-193, XP002281445, ISSN: 0027-5107.

* cited by examiner

*Primary Examiner* — Jim Ketter
(74) *Attorney, Agent, or Firm* — Young & Thompson

(57) ABSTRACT

The invention concerns the use of a mutagenic agent blocking DNA replication in the cell for inserting in vitro a nucleic acid of interest inside a predetermined nucleotide sequence present in a chromosome contained in a prokaryotic or eukaryotic cell, said nucleic acid of interest being, prior to its insertion, included in a DNA vector which replicates in said prokaryotic or eukaryotic host cell.

24 Claims, 3 Drawing Sheets

Figure 1:
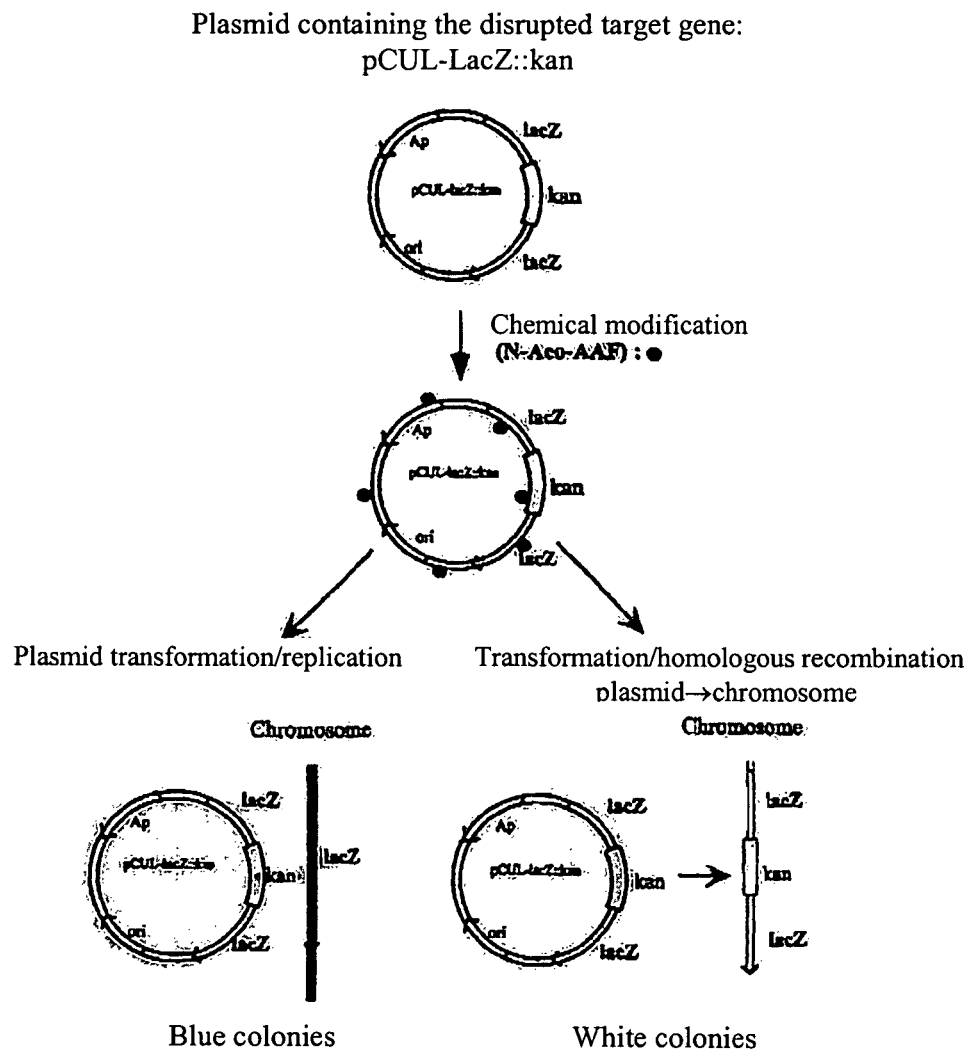

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 1
ggtacaactt gccaactggg                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 2
ttgtcacgtc actcagctcc                                                    20

```
<210> SEQ ID NO 3
<211> LENGTH: 24
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 3
gccggccacg tgatttaaat acgt                                              24

<210> SEQ ID NO 4
<211> LENGTH: 20
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 4
ctttcctgcg ttatcccctg                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 5
tcgccctttg acgttggagt                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 6
agcacttcca cctgatctcc                                                   20

<210> SEQ ID NO 7
<211> LENGTH: 23
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 7
gctcctgtgt tcttcatgct tgg                                               23

<210> SEQ ID NO 8
<211> LENGTH: 20
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 8
gctggccttt tgctcacatg                                                   20

<210> SEQ ID NO 9
```

-continued

```
<211> LENGTH: 20
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 9
aaagggggat gtgctgcaag                                                    20

<210> SEQ ID NO 10
<211> LENGTH: 23
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 10
gcggccacgt gatttaaata cgt                                                23

<210> SEQ ID NO 11
<211> LENGTH: 20
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 11
gctcctgtgt tcatgcttgg                                                    20
```

METHOD FOR INSERTING A NUCLEIC ACID OF INTEREST INTO A PROKARYOTIC OR EUKARYOTIC CELL BY HOMOLOGOUS RECOMBINATION

FIELD OF THE INVENTION

The present invention relates to the field of a targeted insertion of a nucleic acid of interest into a selected location of a genomic nucleic acid being present in a chromosome contained in a prokaryotic or eukaryotic cell.

STATE OF THE ART

Developing efficient and reproducible techniques with a view to a targeted insertion of a nucleic acid of interest into a selected location of a chromosome DNA is currently the object of numerous works, more particularly works relating to the development of somatic cell genic therapy techniques, aiming at preventing or treating human or animal pathologies associated with a deficiency from genetic origin.

Such techniques are useful for treating genetic deficiencies caused by the mutation of the initial wild gene. An example is the cftr gene, some mutations of which lead to the mucoviscidosis disease, also called cystic fibrosis.

The target insertion of a nucleic acid within a chromosomic DNA is also useful within the framework of methods for producing model transgenic animals, more particularly in order to study the physiological effects of the overexpression (<<knock-in>> animals) or on the contrary of the expression blockade (<<knock-out>> animals) of a gene of interest, including in order to develop novel drugs.

Various techniques of targeted insertion of a nucleic acid of interest into a specific and predetermined location of a chromosome DNA are from now available. Various techniques were detailed more, particularly in a review article by CAPECCHI (1989). For example, techniques were disclosed for DNA targeted insertion through homologous recombination by co-transformation of cells with two distinct vectors, respectively a vector containing a selection gene and a vector used for the homologous recombination, such techniques being used more particularly for disrupting a target gene (Reid et al., 1991).

Systems were also disclosed for the homologous recombination with two vectors, respectively (i) a first vector adapted to be integrated into the target genome and providing a single homologous recombination site and (ii) a second vector comprising the sequence of interest to be inserted at the level of the preliminarily integrated single recombination site (U.S. Pat. No. 5,998,144).

Other works deal with homologous recombination systems wherein three molecular partners, respectively (i) a double strand donor DNA fragment, (ii) a first double strand linking DNA, and (iii) a second double strand linking DNA (U.S. Pat. No. 6,207,442).

The use of retroviral vectors for performing the targeted insertion of DNA through homologous recombination was also disclosed (U.S. Pat. No. 6,281,000), as well as the use of vectors comprising two selection marker genes, respectively a negative selection marker and a positive selection marker (U.S. Pat. No. 6,284,541).

Homologous recombination techniques are also known taking advantage of the formation of a DNA three helix type structure at the chromosome location previously selected for the insertion of the DNA of interest, as has been disclosed more specifically in U.S. Pat. Nos. 5,962,426 and 6,303,376.

Techniques were also disclosed for the insertion of genes comprising a transfection step of the target cells with a vector which does not replicate in such cells, also so-called <<suicide vector>>, such suicide vector being preliminarily exposed to a UV irradiation (Hinds et al., 1999).

However, the practice of the above-mentioned homologous recombination techniques, with a view to inserting, in a targeted way, a nucleic acid into a chromosome, illustrates the fact that exogenous DNA sequences of interest transferred into cells, in particular eukaryotic cells, are subjected to homologous recombination events with homologous endogenous sequences of the cell host only at very low recombination frequencies, requiring to turn to the transfection, and then the selection, of a very large number of cells in order to produce at least one clone of recombinant cells for which the DNA sequence of interest has been effectively inserted at the genome selected location.

Additionally, for some of the above-mentioned techniques, the DNA vector(s) used for achieving the homologous recombination is (are) not removed from the cell host, resulting in numerous disadvantages, more specifically as such DNA vectors generally comprise selection genes consisting in resistance genes to various antibiotics, being able to subsequently spread in the recombined prokaryotic or eukaryotic host.

Generally speaking, the gene targeting techniques in higher eukaryotic bodies are faced with the fact that non homologous recombination events are 1000 to 100,000 times more frequent than homologous recombination events. The lack of technique allowing to efficiently increase the homologous recombination frequency oriented research towards the development of homologous recombinant clone enrichment systems based on genetic selections having as for an object to eliminate recombinant clones where non homologous recombination events occurred. However, because of the very low frequency of homologous recombination events and despite the strong selection pressure exerted on recombinant cell clones, it is often very difficult to obtain the desired recombinant clones, all the more in a reproducible way.

DESCRIPTION OF THE INVENTION

The Applicant focussed on developing a method allowing for the targeted insertion of a DNA of interest into a cell chromosome, through homologous recombination, with a high frequency of homologous recombination events, at the end of which the vector carrying the sequence of interest to be targetedly inserted, that could comprise unwanted sequences, such as antibiotic resistance genes, is removed.

It is shown according to the invention that contacting a DNA vector comprising a nucleic acid of interest with a mutagenic agent creating, in said DNA vector, injuries able to interfere with the replication thereof in the cell, allows for the targeted insertion, through a homologous recombination event, of such nucleic acid of interest into a location selected in the genome of said cell, with a high frequency of the homologous recombination event.

Simultaneously, the parts of the DNA vector, other than the nucleic acid of interest being initially included in the latter, are removed from the recombined prokaryotic or eukaryotic host cell.

Therefore, according to the invention, it has been shown that the use of a DNA vector comprising a nucleic acid of interest, said vector replicating in target prokaryotic or eukaryotic cells, allows, when the DNA vector is treated with a mutagenic agent prior to a transfection step in the cells, to obtain a high frequency of homologous recombination events resulting in the targeted insertion of said nucleic acid of interest into a selected location of the cell genome.

Without wishing to be bound by any theory, the Applicant believes that the high frequency of homologous recombination events, and thus, the high frequency of insertion of the nucleic acid of interest into the genome of target cells, is due to the creation, at the time of the replication of the DNA vector in the transfected cells, of highly recombinogenic neosynthesized DNA ends. Thus, by means of the treatment of the DNA vector by the mutagenic agent, the replication of the vector in the cell is blocked at the level of injuries caused by such a mutagenic agent on the DNA of the vector, leading to the production of newly synthesized DNA fragments having the ends able to recombine with the chromosomal target DNA, through non reciprocal homologous recombination events of the vector towards the target chromosome in the cell.

This is the reason why the mutagenic agents according to the invention are selected amongst agents blocking the DNA replication in the procaryotic or eukaryotic cell and thereby creating recombinogenic structures within the DNA treated by said mutagenic agents.

It meant by recombinogenic structure one or more regions of the treated DNA wherein the double strand DNA structure is affected, for example, through the creation of a mismatch of the bases, including an possible cut of one of the DNA strands. Such DNA recombinogenic structures are created during the disruption of the DNA synthesis because of the initial treatment with the selected mutagenic agent and include, unexhaustively, single strand breaks, single strand breaches, as well as double strand breaks.

In particular, it is shown according to the invention that contacting the DNA vector comprising a nucleic acid of interest with the N-acetoxy-2-acetylaminofluorene (N-AcO-AAF) mutagenic agent could allow for the targeted insertion of such an DNA of interest into a selected location of a chromosome DNA contained in a cell, through homologous recombination of the vector towards the chromosome, with a high occurrence frequency of the homologous recombination event.

Binding the N-AcO-AAF molecules onto the polynucleotide comprising the DNA of interest allows for obtaining non reciprocal homologous recombination events from the DNA vector to the chromosome, with a frequency likely to be higher than 0.05 homologous recombination events per transfected cell.

An object of the invention is therefore the use of a mutagenic agent blocking the DNA replication in the cell for in vitro inserting a nucleic acid of interest within a predetermined nucleotide sequence being present in a chromosome contained in a prokaryotic or eukaryotic cell, said nucleic acid of interest being, prior to its insertion, included into a DNA vector replicating in said prokaryotic or eukaryotic host cell.

A mutagenic agent blocking the DNA replication in the cell encompasses, according to the invention, any natural or synthetic chemical compound, as well as an ultraviolet (UV) irradiation, having its blocking activity of the DNA replication likely to be determined by any technique known to the man of the art, for example, the technique as described by FUCHS (1984), using the 5'->3' exonuclease activity of the DNA polymerase of the T4 phage, which is blocked at the vicinity of the chemically modified bases.

Advantageously, the mutagenic agent is selected amongst N-AcO-AAF, alkylating agents, benzo(a)pyrene-diol-epoxide (BPDE), as well as UV irradiation.

When the mutagenic agent consists in a UV irradiation, the DNA to be treated is advantageously irradiated by a UV beam source immediately before this DNA is used for transfecting cells. For example, the DNA could be adjusted to the concentration of 100 µg/ml in a TE buffer (pH 8.0) then irradiated at a temperature ranging form 20° C. to 25° C. at a power of 1.8 $J.m^{-2}.s^{-1}$ using a germicidal lamp, for example, the lamp so-referred to G8T5 (General Electric).

Preferably, the mutagenic agent is N-acetoxy-2-acetylamino-fluorene (N-AcO-AAF).

The N-AcO-AAF compound is known in the art as a mutagenic agent. The N-AcO-AAF compound has more specifically been used within the framework of academic works relating to the study of the DNA repair mechanism in bacterial cells. When the N-AcO-AAF compound is being contacted with a bacterial plasmid being subsequently transfected in *Escherichia coli* cells, some induction of the DNA repair intracellular mechanisms is observed, which, through excision and elongation steps of the cleaved DNA, allow for the survival of the plasmid in *E. coli* cells (Schmid et al., 1982).

It has also been shown that the frequency of some homologous recombination events, from the chromosome to the plasmid, could be increased when the plasmid is preliminarily treated with N-AcO-AAF, in an *Escherichia coli* cell system.

So, Luisi-DeLuca et al. (1984) use a plasmid carrying the $lacY^+$ gene in a bacterial host of the $LacY^-$ phenotype. After transformation of the bacterial cell by the plasmid, most of the transformed bacteria are of the $Lac^-$ phenotypes. The resulting $Lac^-$ transformants originate from a transfer of the $lacY^-$ allele from the chromosome to the plasmid.

Maher et al. (1990) also showed that the N-AcO-AAF induces intrachromosome homologous recombination events between genes being present in mouse's cells, within the framework of an academic study on the cancer induction mechanisms by mutagenic agents.

It has been shown for the first time according to the invention that a mutagenic agent such as hereinabove defined, more particularly the N-AcO-AAF compound, when contacted with a replicative DNA vector comprising a DNA of interest to be inserted in a targeted way into the chromosome of a prokaryotic or eukaryotic cell, is able to induce a transfer of the DNA of interest from said vector, which could be for example a plasmid, to the chromosome, and this, with a very high frequency of the non reciprocal homologous recombination events from the polynucleotide to the chromosome.

Therefore, an object of the invention is also to provide a method for in vitro inserting a nucleic acid of interest initially included in a DNA vector, within a predetermined nucleotide sequence present in a chromosome contained in a prokaryotic or eukaryotic cell, characterized in that it comprises the following steps of:

a) contacting the DNA vector comprising the nucleic acid of interest, and which replicates in said prokaryotic or eukaryotic cell, with a mutagenic agent blocking the DNA replication in the cell;

b) transfecting prokaryotic or eukaryotic cells with the DNA vector such as obtained at the end of step a); and c) selecting the prokaryotic or eukaryotic cells for which the nucleic acid of interest has been integrated into the predetermined nucleotide sequence.

Preferably, the above-mentioned method further comprises the following step of:

d) selecting, amongst the prokaryotic or eukaryotic cells as selected in step c), the cells wherein the DNA vector sequences, other than those of the nucleic acid of interest, were removed.

Advantageously, the N-AcO-AAF compound is prepared through chemical synthesis from nitrofluorene, using techniques known to the man of the art, such as, for example, the technique being described by LEFEVRE et al. (1978).

The starting nitrofluorene, as well as the final N-AcO-AAF compound, could be supplied, inter alia, by AMERSHAM company.

It has been shown, according to the invention, that the frequency of non reciprocal homologous recombination events from the DNA vector, for example a plasmid, to the chromosome, increases with an increasing number of injuries or chemically modified bases caused by the mutagenic agent in said DNA vector.

For example, it has been shown according to the invention that the frequency of non reciprocal homologous recombination events from the DNA vector, for example, a plasmid, to the chromosome, increases with an increasing number of mutagenic agent molecules, such as the N-AcO-AAF, bound to said DNA vector.

Thus, the frequency of homologous recombination events switches from $5.61 \times 10^{-4}$ for ten molecules of N-AcO-AAF per molecule of the DNA vector comprising the nucleic acid of interest to more than $600 \times 10^{-4}$ for 67 molecules of N-AcO-AAF per molecule of the DNA vector comprising the nucleic acid of interest.

Increasing frequencies of non reciprocal homologous recombination from the DNA vector to the chromosome could be reached with even higher ratios of DNA injuries or the number of mutagenic agent molecules, such as the N-AcO-AAF, per molecule of said vector.

Thus, the number of injuries of the DNA or the mutagenic agent molecules per molecule of the DNA vector comprising the nucleic acid of interest could exceed 100/1.

Advantageously, in step a) of the method, the final concentration of the mutagenic agent to be used is adapted to the attachment of at least 10 molecules of mutagenic agent per molecule of the DNA vector. More preferably, the final concentration of the mutagenic agent to be used is adapted to the attachment of at least 50 molecules of such a mutagenic agent per molecule of the DNA vector.

According to the invention, the number of mutagenic agent molecules, more particularly of N-Aco-AAF, per molecule of the DNA vector comprising the nucleic acid of interest is at least 10/1 and could increase beyond 100/1, for example, as high as 200/1.

Advantageously, the number of mutagenic agent molecules per molecule of the DNA vector comprising the nucleic acid of interest ranges from 10/1 to 100/1, the optimal ratio of the number of mutagenic agent molecules to the molecules of said DNA vector being selected as a function of the desired frequency of the non reciprocal homologous recombination from the vector to the chromosome.

In order to achieve the desired mutagenic agent/DNA vector molar ratio, the man of the art could vary (i) the relative concentrations of said mutagenic agent and said vector being contacted in step a) of the method and/or (ii) the duration of the contacting step a) of said mutagenic agent with said vector.

Preferably, for a given DNA vector, with a given size, the mutagenic agent/DNA vector molar ratio is varied by modifying the duration of the contacting step a) between said mutagenic agent and said vector.

Similarly, for achieving a given mutagenic agent/vector molar ratio, the duration of step a) is varied depending on the size of the DNA vector being considered, the duration of step a) being all the longer as the size of the DNA vector is larger.

The man of the art could easily determine whether, at the end of step a) of the method, the desired mutagenic agent/DNA vector molar ratio has been reached according to conventional techniques.

For example, at the end of step a), an aliquot of the mutagenic agent/vector mixture is taken and the free mutagenic agent molecules are removed, for example, through a DNA precipitation followed by a filtration on a nitrocellulose filter.

Then, the number of vector mols and the number of mutagenic agent mols bound on said vector are respectively determined in order to establish the mutagenic agent/vector ratio being reached.

The number of DNA vector mols contained in the aliquot could be traditionally determined through UV spectrophotometry at a wavelength of 260 nanometers.

The number of mutagenic agent mols bound on this DNA vector could be determined through radioactivity measurement, for example, when, for trials, a mutagenic agent has been used being labelled with a radioactive isotope such as $^3[H]$.

A mutagenic agent molecule binds onto the vector base. The result could be therefore expressed as a percentage of bases of the DNA vector which have been modified by the mutagenic agent.

For example, it has been determined, according to the invention, when a vector has been treated, for example, a plasmid, being 5,000 pair of bases long, that the mutagenic agent/vector molar ratios were respectively 13 (0.26% of modified bases) for a duration of step a) of 4 minutes, 28 (0.36% of modified bases) for a duration of 8 minutes, and 56 (1.12% of modified bases) for a duration of 20 minutes, after contacting 60 µg of the DNA vector in solution with 1.2 µg of N-AcO-AAF.

For implementing step a) of the method, the vector comprising the nucleic acid of interest is advantageously suspended in a salt buffer, preferably a citrate buffer, optionally added with ethanol.

The mutagenic agent is in solution in an appropriate solvent. In the case of the N-AcO-AAF, ethanol is preferably used.

For a given trial, the man of the art will adapt the mutagenic agent/DNA vector molar ratio, by means of simple routine trials, until the optimum frequency of desired homologous recombination events being looked for has been reached.

As used herein, it is meant by <<DNA vector>> a circular or linear DNA molecule being indiscriminately in either a single strand or a double strand form, and replicating in the prokaryotic or eukaryotic host cell wherein such DNA vector should be transfected.

Preferably, the DNA vector according to the invention is a vector being able to be replicated in a selected cell host, for example, a bacterial cell and even more specifically, an *Escherichia coli* cell, so as to produce large amounts thereof in the host cells. Once the DNA vector is obtained in a sufficient amount for performing the transfection step in the selected host cell, such a vector is used as a starting material for the targeted insertion, into the cell genome, of the nucleic acid of interest being inserted in the latter.

A DNA vector for implementing the method according to the invention comprises, in addition to the nucleic acid of interest, also at least a functional replication origin in the host cell wherein it is to be transfected with a view to a targeted insertion, through homologous recombination, of the nucleic acid of interest in such a vector. A DNA vector according to the invention comprises 1, 2, 3, 4 or 5 functional replication origins in the host cell wherein it is to be transfected with a view to the targeted insertion of the nucleic acid of interest in the selected prokaryotic or eukaryotic host cell.

When the host cell to be transfected is a prokaryotic cell, for example a bacterial host cell, and even more specifically an *Escherichia coli* cell, the DNA vector comprises at least one functional replication origin in such a prokaryotic cell, for example a functional replication origin in *Escherichia coli*.

When the host cell to be transfected is an eukaryotic cell, for example a mammal's host cell, and even more specifically a human cell, the DNA vector comprises at least one functional replication origin in such an eukaryotic cell, for example a functional replication origin in human cells.

Advantageously, such a vector also comprises the sequence of a marker gene, for example an antibiotic resistance gene, allowing for the selection of host cells, including *E. coli* host cells, which have been transfected with said vector, such transfected cells allowing, through their culture in an appropriate culture medium, for large amounts of the vector to be obtained.

Advantageously, such a vector also comprises the sequence of a functional marker gene in the host cell wherein the insertion of the nucleic acid of interest is looked for through homologous recombination, the detection of the expression of said marker gene allowing for the positive or negative selection of host cells that have been actually transfected with such a vector.

A first preferred illustration of a vector making up the DNA vector comprising the nucleic acid of interest used according to the invention is the pCUL-lacZ :kan vector, the building method of which is described in the examples.

A second preferred illustration of a vector making up the DNA vector comprising the nucleic acid of interest used according to the invention is the pGT-rev1 vector, the building method of which is described in the examples.

Vectors could optionally be used being able to include large insertion sequences. In this particular embodiment, bacteriophage vectors will be preferably used, such as P1 bacteriophage vectors, such as the p158 vector as well as the p158/neo8 vector described by Stemberg (1992, 1994).

The preferred bacterial vectors according to the invention are, for example, the pBR322 (ATCC37017) vectors as well as vectors such as pAA223-3 (Pharmacia, Uppsala, Sweden), and pGEM1 (Promega Biotech, Madison, Wis., United States of America).

Other vectors available on the market could be mentioned, such as the pQE70, pQE60, pQE9 (Qiagen), psiX174, pBluescript SA, pNH8A, pNH16A, pNH18A, pNH46A, pWL-NEO, pSV2CAT, pOG44, pXTI, pSG(Stratagene) vectors.

It may also be the PXP1recombinant vector such as disclosed by Nordeen SK et al. (1988).

There could also be adenoviral vectors such as the human adenovirus of the 2 or 5 type.

A recombinant vector according to the invention could also be a retroviral vector as well as an adeno-associated vector (AAV). Such adeno-associated vectors are disclosed, for example, by Flotte et al. (1992), Samulski et al. (1989), or even by McLaughlin B A et al. (1996).

According to another embodiment of the polynucleotide comprising the nucleic acid of interest, the DNA vector is a double strand linear DNA.

Surprisingly, it has been shown that the method of the invention allows for the targeted insertion of large sized nucleic acids, higher than 1.5 kilobases. Such a feature of the method of the invention is particularly advantageous, as it more specifically allows for the targeted insertion of genome sequences of complete genes, with all the functional sequences being present in the gene introns, which are not to be found, for example, in the corresponding cDNA.

Generally speaking, the nucleic acid of interest to be inserted into the genome of the prokaryotic or eukaryotic cell included in the DNA vector comprises at least, respectively at its end 5' and at its end 3', nucleotide sequences with a high identity degree, preferably higher than 99.5%, or more preferably, higher than 99.6%, 99.7%, 99.8%, 99.9% identity, without any deficiency or <<gap>>, with the corresponding sequences of the target DNA contained in the chromosome. Preferably, such sequences being respectively located at the ends 5' and 3' of the nucleic acid of interest are identical to the sequences of the respective ends 5' and 3' of the aimed at target sequence being present in the chromosome, in order to further increase the frequency of homologous recombination events. The flanking sequences respectively located at the ends 5' and 3' of the nucleic acid of interest included in the vector used for transfection comprise at least 100 pairs of bases, preferably at least 300 pairs of successive bases identical to the corresponding target sequences in the chromosome. The larger the size of the 5' and 3' flanking sequences, the higher the probability to obtain a high homologous recombination frequency. In general terms, flanking sequences are preferred with from 300 to 1,500 pairs of identical bases with the corresponding native target sequences in the chromosome.

Homologous flanking sequences longer than 1,500 pairs of bases could also be used.

According to a most preferred embodiment of the method, the nucleic acid of interest to be inserted into the genome, being included in the DNA vector, comprises a selection marker sequence. Preferably, the selection marker nucleotide sequence consists in a selection marker gene expressing in the prokaryotic or eukaryotic host cell after the targeted insertion, through homologous recombination, of said nucleic acid of interest at the genome selected location. Advantageously, the selection marker gene is selected amongst:

a) selection marker genes being functional in *E. coli*, such as ampicillin, tetracycline, kanamycin and chloramphenicol resistance genes;

b) marker genes being functional in mammalian cells, such as neomycin or zeocin resistance genes;

c) marker genes coding a fluorescent protein such as a GFP (<<Green Fluorescent Protein>>) or YFP (<<Yellow Fluorescent Protein>>).

In order to select an appropriate selection marker gene, the man of the art should advantageously refer to the works by Sambrook et al. (2001).

The selection marker gene included in the nucleic acid of interest thus readily allows to perform the step c) selection of the method according to the invention.

Indeed, the selection marker sequence included in the nucleic acid of interest makes easy the selection of clones of prokaryotic or eukaryotic cells initially transfected with the DNA vector comprising said nucleic acid of interest, which cells have integrated, through homologous recombination, said nucleic acid of interest, in the selected location of their genome. The non reciprocal homologous recombination event from the vector to the chromosome could thus be detected through the observation of the phenotype of the recombined prokaryotic or eukaryotic cells, said phenotype being imparted by the expression of the marker gene, for example for the production of a marker protein coded by the marker gene. The marker protein may be an antibiotic resistance protein as well as a fluorescent protein.

According to a first preferred aspect, the nucleic acid of interest being contained in the vector comprises an open reading frame coding a protein of therapeutic interest. The protein of therapeutic interest could be of any nature. It could be for example a protein selected amongst cytokines, hormones or also growth factors.

Examples of cytokines are Interleukins, such as IL-1, IL-2, IL-3, IL-4, IL-5, IL6, IL-10 or IL-12, as well as other cytokine factors such as MG-CSF.

Examples of hormones are more specifically LHRH. Amongst growth factors is to be mentioned, amongst others, the human growth hormone.

The protein of therapeutic interest could also be a protein or an antigenic peptide able, when being presented to the immune system cells, to induce the production of antibodies towards an antigen, for example an antigen derived from a bacterium or a pathogenic virus, or also to induce the production of specific T-cytotoxic lymphocytes of an antigen derived from a pathogenic body, such as a retrovirus as HIV-1 or HIV-2 or the viral hepatitis virus, as well as specific T-cytotoxic lymphocytes of tumoral antigens.

Preferably, according to this first preferred aspect of the nucleic acid of interest, the open reading frame codes a protein of therapeutic interest having an overexpression thereof being looked at in a host cell.

According to a second preferred aspect, the nucleic acid of interest comprises an open reading frame disrupted by a heterologous nucleotide sequence. Such a second preferred aspect of the invention is mainly implemented when the targeted insertion of the nucleic acid of interest aims at replacing, in the cell chromosome, at least part of the sequence of a gene by said nucleic acid of interest, so as to disrupt the native wild sequence of said gene in the chromosome and thereby block its expression. Such a nucleic acid comprises at least, from the end 5' to the end 3', (i) a first nucleotide sequence identical to a sequence of the target gene present in the chromosome, (ii) the heterologous nucleotide sequence, and (iii) a second nucleotide sequence identical to a second sequence of the target gene in the chromosome. The nucleotide sequences (i) and (ii), being identical to corresponding sequences in the chromosome, allow for the insertion of the nucleic acid of interest to be targeted in said gene.

According to the invention, the heterologous nucleotide sequence (ii) consists in a nucleotide sequence which is not naturally present in the target DNA aimed at.

This preferred second aspect of the nucleic acid of interest will be particularly used for transfecting embryo strain cells of non human mammals, in a method for producing transgenic animals wherein the target gene is disrupted and blocked in its expression (knock-out animals).

According to this second preferred aspect, the heterologous nucleotide sequence (ii) could be a marker gene as previously defined, such as a gene coding an antibiotic resistance protein as well as another detectable protein, such as a fluorescent protein as GFP (<<Green fluorescent protein>>) as well as YFP (<<Yellow fluorescent protein>>), well known to the man of the art.

According to a third preferred aspect, the nucleic acid of interest codes an antisense RNA. This third preferred aspect of the nucleic acid of interest will be implemented when the objective aimed at is to inhibit the expression of a protein coded by a target gene, the thus produced antisense RNA specifically hybridizing with the messenger RNA making up the gene transcription product, the expression inhibition of which is being looked at.

According to a fourth preferred aspect, the method according to the invention is used for inserting one or more mutations into a genome sequence of a prokaryotic or eukaryotic cell, for example one or more point mutations each corresponding to the substitution of a base in the initial targeted genome sequence of the prokaryotic or eukaryotic cell. According to this fourth preferred aspect, the nucleic acid of interest included in the DNA vector has a nucleotide sequence identical to that of the targeted genome sequence, except for the substituted base(s).

Preferably, according to this fourth preferred aspect, the heterologous bases as compared to the target sequence of the cell genome, being included in the nucleic acid of interest, are advantageously located at the vicinity of the selection marker sequence also included in the nucleic acid of interest.

Most preferably, the nucleic acid of interest comprises, according to such a fourth embodiment, from 1 to 10 substituted bases, distinct from the corresponding bases of the target DNA aimed at.

Such a fourth embodiment is applied more specifically for correcting or on the contrary for inserting specific mutations, in a targeted way, into predetermined locations of the cell genome, for example in methods for obtaining transgenic animals of the <<knock-in>> type.

More preferably, the nucleic acid of interest included in the DNA vector further comprises a nucleotide sequence with a promoter function, being functional in the selected prokaryotic or eukaryotic host cell, under the control of which the open reading frame or the sequence coding the antisense DNA is arranged. The promoter type will be selected amongst known promoters, depending on the selected host cell type, either prokaryotic or eukaryotic.

By way of examples, the bacterial promoters could be the promoters LacI, LacZ, the promoters of RNA polymerase of the T3 or T7 bacteriophage, the promoters PR or PL of the lambda phage.

The promoters for eukaryotic cells will comprise the promoter of the thymidine kinase of the HSV virus or also the promoter of the mouse's metallothionein-L.

Generally, for selecting an adapted promoter, the man of the art could advantageously refer to the works by Sambrook et al. (1989) or also to the techniques as disclosed by Fuller et al. (1996).

According to still another preferred embodiment of the invention, the DNA vector comprising the nucleic acid of interest being used for transfecting eukaryotic or prokaryotic cells, comprises a marker nucleotide sequence, more specifically a marker gene, for example a nucleotide sequence coding a marker protein, said nucleotide sequence being located, in said vector, outside the nucleotide sequence of the nucleic acid of interest. Such a marker gene readily allows for performing the step d) selection of the method according to the invention. According to this preferred embodiment of the invention, the expression of the marker protein coded by the nucleotide sequence located outside the sequence of the nucleic acid of interest allows to select prokaryotic or eukaryotic host cells that have been efficiently transfected by said DNA vector, for example a plasmid or any other DNA vector, but for which the homologous recombination event did not occur with the removal of the nucleotide sequences of the vector, other than that of the nucleic acid of interest, for example, with the removal of sequences of the vector other than those of the nucleic acid of interest to be inserted.

Inserting the DNA vector comprising the nucleic acid of interest according to the invention into a cell occurs in vitro, according to techniques well known to the man of the art for transforming or transfecting cells, either in a primary culture, or in the form of cell lineages.

For inserting vectors into a host cell, the man of the art could advantageously refer to various techniques, such as the calcium phosphate precipitation technique (Graham et al., 1973; Chen et al., 1987), the DEAE Dextran (Gopal, 1985), the electroporation (Tur-Kaspa, 1896), the direct microinjection (Harland et al., 1985), or also DNA charged liposomes (Nicolau et al., 1982, Fraley et al., 1979).

The method according to the invention finds a preferred application for the targeted insertion of the nucleic acid of interest in a bacterial cell or in a mammalian cell, either human or non human.

When the method according to the invention is implemented for the targeted insertion of a nucleic acid of interest into the genome of a mammalian cell, more particularly into a predetermined location of the genome of a human cell, it is integrated as a particular step for performing a genic therapy method for somatic cells.

The genic therapy consists in correcting a deficiency or an anomaly (mutation, aberrant expression, etc.) or ensuring the expression of a protein of therapeutic interest through the insertion of genetic information into the affected cell or body. Such genetic information could be inserted either ex vivo into a cell extracted from the body, the modified cell being then reinserted into the organism, or directly in vivo into the appropriate tissue. In this latter case, there exist various techniques, amongst which various transfection techniques involving DNA and DEAE-dextran complexes (Pagano et al., 1967), DNA and nuclear protein complexes (Kaneda et al., 1989), DNA and lipid complexes (Felgner et al., 1987), the use of liposomes (Fraley et al., 1980), etc. More recently, the use of viruses as vectors for transferring genes has been found to be a promising alternative to physical transfection techniques. In this respect, various viruses were tested for their ability to infect some cell populations, more particularly, retroviruses (RSV, HMS, MMS, etc.), HSV virus, adeno-associated viruses and adenoviruses.

According to still another preferred aspect, the cells transfected in step b) of the method of the invention comprise bacterial cells such as E. coli.

In another preferred aspect, the cells transfected in step b) of the method of the invention consist in non human mammalian cells, such as mouse or rabbits' cells, including embryo strain cells of the ES lineage, as well as rats', guinea-pigs', dogs' or monkeys' cells.

According to a last preferred aspect of the invention, the cells transfected in step b) of the method consist in human cells, as for example epithelial cells, muscle cells, monocytes/macrophages or also lymphocytes.

The present invention is further illustrated, without any limitation, by the figures and the following examples.

FIG. 1 illustrates the experimental scheme of the insertion of a nucleic acid of interest containing the LacZ gene disrupted by a kanamycin resistance marker gene in the genome of an *Escherichia coli* cell.

Figure 2:
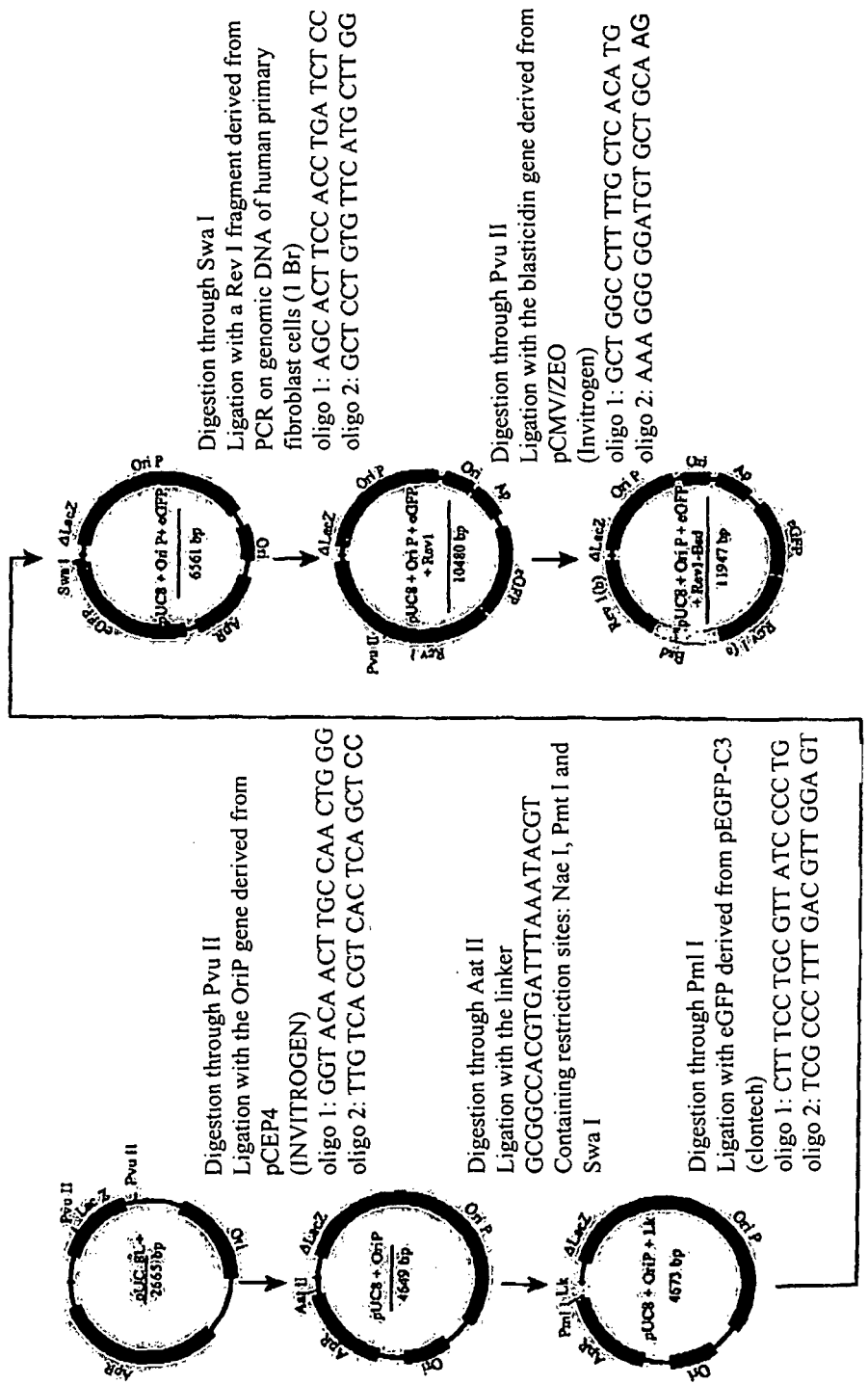

Fig. 2 illustrates the building experimental scheme of a DNA vector for the targeted insertion of a nucleic acid of interest into human cells, the pGT-Rev1 vector. In the pGT-Rev1 vector, the nucleic acid of interest is the Rev1 nucleic acid coding a human polymerase, having its sequence disrupted by a marker gene, herein the Zeocin resistance gene or the Blasticidin resistance gene (SEQ ID NOS 1-2, 10, 4-6, 11, and 8-9 disclosed respectively in order of appearance).

Figure 3:
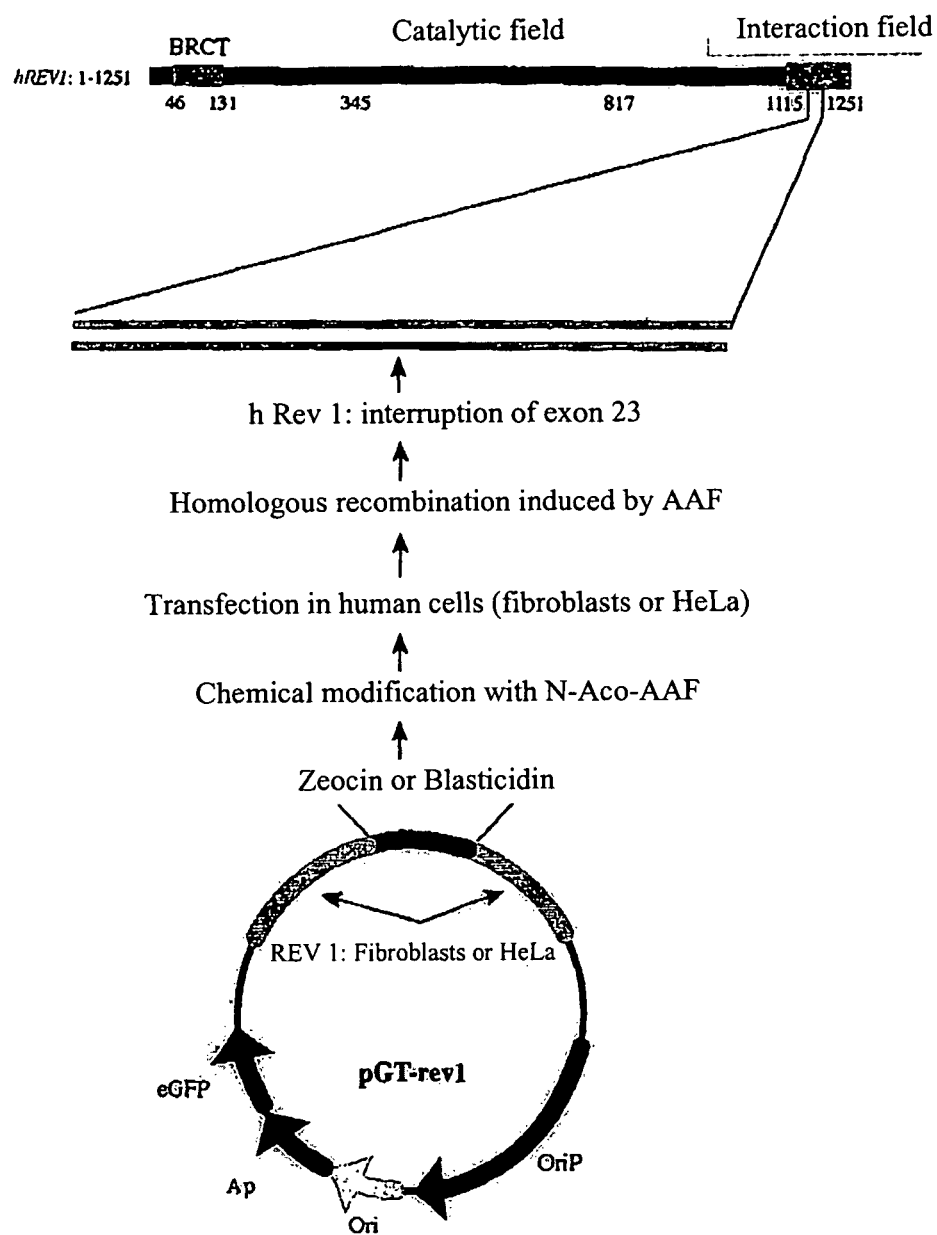

FIG. 3 illustrates the in vitro transfection scheme of human cells with the pGT-Rev1 vector, with a view to inserting into the chromosome a non functional copy of the Rev 1 gene, disrupted by the marker gene.

EXAMPLES

Example 1

Building the pCUL-lacZ::kan vector

The pCUL-LacZ::kan plasmid was built from a well known pUC8 vector derivate (as disclosed by YANNISCH-PERRON et al.,1985) wherein the replication origin as well as the LacZ' gene were inverted (pCUL-vector, cf Schumacher et al. 1998). The LacZ gene was obtained through treatment of a derivate of the pBR329 plasmid containing the LacZ gene by means of <<fill-in>> EcoRI and FspI restriction endonucleases. The thus obtained 3000 bp fragment was then cloned into the SapI sites (filled in) in FspI of the pCUL-vector. The resulting plasmid (pCUL-LacZ) contains the ColEI replication origin, the ampicillin resistance marker as well as the whole lacZ gene. The kanamycin resistance gene, cloned by PCR from the pUC4k vector (Pharmacia) has then been inserted into the EcoRV site of the pCUL-LacZ plasmid for giving rise to the pCUL-LacZ::kan plasmid used in the sequence of experiments.

Example 2

Targeted Insertion, Through Homologous Recombination, of a Nucleic Acid of Interest into a Prokaryotic Cell Genome A. Material and Methods A.1 Treatment of the Vector by the N-AcO-AAF Reaction mixture Plasmid DNA: Final concentration of 0.5 µg/µl in $2\times10^{-3}$ M citrate buffer, pH 7

N-AcO-AAF: Final concentration of 400 µg/ml in ethanol.

60 µg DNA are added in 114 µl of $2\times10^{-3}$ M citrate buffer, pH7, added with 3 µl of ethanol at 100%.

The solution is preheated at 37° C.; then 3 µl of N-AcO-AAF (400 µg/ml) are added, marked with tritium ($^3$H).

Reaction time: 4, 8, 20 minutes.

40 µl are taken at the various selected times. The reaction is stopped by a DNA precipitation step with 3 volumes of ethanol/sodium acetate 0.16M followed by three other precipitation steps under the same conditions.

The percentage of modified bases is determined measuring the number of plasmid mols through UV spectrophotometry and the number of bound AAF mols, through βradioactivity counting.

The result is expressed in percentage of modified bases. The reaction time is adapted as a function of the size of the plasmid and the desired percentage of modified bases.

A.2. Performing Transfection of *E.coli* Cells

*E. coli* cells are transformed following the conventional electroporation method by using the conditions recommended by the device manufacturers to this end (Gene Pulser from Biorad for example).

A.3. Selection of Recombinant Cell Clones

In the example, transformant clones are selected on a LB-agar medium containing kanamycin (20 µg/ml) and the lack of β-galactosidase activity (being expressed by white colonies instead of blue ones), i.e. a phenotype typical of a non reciprocal recombination event is visualized by means of the presence of X-gal (5-bromo-4-chloro-3-indolyl-β-D-galactopyranoside) and IPTG (isopropyl-β-D-thiogalactopyranoside) in the dishes.

B. Results

The results are presented in table I hereinbelow.

TABLE I

| Number of injuries per plasmid | Recombination frequency: white colonies/total colonies |
|---|---|
| 0AAF | <0.0096[a] |
|  | 10426/0[b] |
| 10AA2F | 0.056 |
|  | 17819/10 |
| 20AAF | 0.17 |
|  | 9692/17 |
| 33AAF | 0.32 |
|  | 2301975 |
| 43AAF | 1.41 |
|  | 16554/237 |
| 67AAF | 6.07 |
|  | 1934/125 |

[a]Homologous recombination frequency
[b]Total number of colonies/number of recombined colonies.

The results as presented hereinabove in table I clearly indicate that the targeted homologous recombination frequency increases depending on the number of injuries produced by the chemical modification of the plasmid (table I). Thus, in a wild strain for recombination systems, while homologous recombination spontaneous events account for less than 0.03% of the transformation events, the presence of 67 AAF injuries on such a plasmid results in obtaining more than 6% of targeted recombinant molecules, i.e. a more than 1,700 fold increase in the recombination frequency.

Moreover, it has been focussed that with the method of the invention, the mechanism leading to a gene targeting is a non reciprocal homologous recombination mechanism during which the plasmid molecule is lost. This makes it possible to achieve a very efficient gene targeting within one single step. In *E. coli*, such method was used for building more than ten strains wherein different genes were disrupted.

Thus, for example, strains were built wherein some genes involved in the recombination (recF, recG, dinG) were disrupted by genes coding the resistance to antibiotics such as tetracycline or chloramphenicol. Such a gene targeting was achieved in different genetic backgrounds such as for example in strains having their excision repair system (uvrABC dependent) inactivated.

Example 2

Targeted Insertion, Through Homologous Recombination, of a Nucleic Acid of Interest in a Human Eukaryotic Cell Genome A. Building the PGT-Rev1 Vector The pGT-Rev1 vector intended to be used in the method according to the invention has been built up in order to insert a non functional copy of the Rev1 gene into the genome of a human cell, as a replacement of the native Rev1 gene copy.

The pGT-Rev1 vector comprises a functional replication origin in *E. coli*, here the ColE1 origin, allowing, after *E. coli* cells have been transfected with this vector, to obtain sufficient amounts of the vector so as to subsequently transfect target human cells, in order to insert the Rev1 gene disrupted by the marker gene, instead of the native Rev1 gene. In order to check how successful the transfection in *E. coli* is, the PGT-Rev1 vector comprises a selection marker gene being functional in bacteria, the ampicillin resistance gene.

The pGT-Rev1 vector comprises a replication origin functional in human cells, herein the oriP replication origin of the Epstein-Barr virus, allowing for the vector to replicate a limited number of times in human cells. In order to check how successful the transfection in human cells is, the PGT-REV1 vector comprises a transfection marker gene being functional in man, the eGFP gene coding the <<Green Fluorescent Protein>>.

The different steps of the building protocol for the pGT vector are described on the scheme in FIG. 2. It is obvious to the man of the art that the nucleic acid of interest is inserted into the pGT vector as described on FIG. 2, for obtaining the DNA vector used in the method of the invention. More specifically, FIG. 3 illustrates the PGT-Rev1 vector being the pGT vector into which has been inserted, as the nucleic acid of interest, the Rev1 human vector having its nucleotide sequence being disrupted by a marker gene.

As illustrated on FIG. 2, for achieving the pGT vector, the following oligonucleotides were used:

a)
Step 1:
oligo 1:    GGTACAACTTGCCAACTGGG;       (SEQ ID No. 1)

oligo 2:    TTGTCACGTCACTCAGCTCC;       (SEQ ID No. 2)

b)
Step 2:
            GCCGGCCACGTGATTTAAATACGT;   (SEQ ID No. 3)

c)
Step 3:
oligo 1:    CTTTCCTGCGTTATCCCCTG;       (SEQ ID No. 4)

oligo 2:    TCGCCCTTTGACGTTGGAGT;       (SEQ ID No. 5)

d)
Step 4:
oligo 1:    AGCACTTCCACCTGATCTCC;       (SEQ ID No. 6)

oligo 2:    GCTCCTGTGTTCTTCATGCTTGG;    (SEQ ID No. 7)

e)
Step 5:
oligo 1:    GCTGGCCTTTTGCTCACATG;       (SEQ ID No. 8)

oligo 2:    AAAGGGGATGTGCTGCAAG.        (SEQ ID No. 9)

Using the principle developed in *E. coli*, the tool described in the previous examples was adapted for the transfection of cultured human cells.

To this end, a vector has been developed with the following characteristics: i) it is able to replicate in the bacterium so that sufficient plasmid can be produced in order to modify it chemically; ii) it is also able to replicate in human cells so as to generate recombinogenic ends through blockade of the replication at the injury level. Consequently, the backbone of such a vector contains the following elements:

Replication origin operating in *E. coli* (ColE1, large number of copies),

Bacterial selection marker: ampicillin resistance,

Replication origin of the Epstein-Barr (oriP) virus allowing it to replicate a limited number of times in human cells, Transfection marker: Green Fluorescent Protein (eGFP).

B. Targeting of the Human REV1 Gene

The product of the REVI gene belongs to a new class of dedicated polymerases (to which also belong the DNA polymerases eta (Polη), iota (Polι) and kappa (Polκ)) having as a characteristic the particular structure of their active site allowing them to tolerate and replicate the DNA containing injuries or distortions. It has been recently shown in the Applicant's lab that the protein coded by the REV1 gene and the eta DNA polymerase interact and the region of such an interaction on the Rev 1 protein has been mapped. Polη plays a paramount part in the cell as it is able to very efficiently cross and without any error a T-T pyrimidine dimer of the cyclobutane type (injury predominantly formed after cell irradiation to ultraviolet rays). The lack of such a polymerase is at the origin of the *Xeroderma pigmentosum* disease variant (XPV) and leads to the hypermutability of cells after UV irradiation and the occurrence of skin cancers.

While the interaction between Rev1 and Polη is confirmed, its physiological part remains unknown and having available a Rev1 mutant no longer interacting with Polη would obviously enable to understand the extent of such an interaction.

The Applicant targeted the interaction site carried by Rev1, using the following strategy:

a) Amplification by PCR of the chromosome fragment containing the exon 23 of the Rev1 gene, derived either from 1BR cells (primary fibroblasts) or from HeLa cells (transformed human cells); sequencing of the PCR product and cloning in suitable plasmids so as to have two alleles available on the plasmid;

b) Interruption of the exon 23 of each allele cloned by a gene coding the antibiotic resistance (blasticidin or zeocin);

c) Modification of the thus obtained plasmids by the N-Aco-AAF; and d) Transfection in cultured human cells (1Br or Hela) and selection for the resistance towards the selected antibiotic.

Results

A series of experiments were conducted: plasmids containing the REV1 gene fragment derived from primary fibroblasts (1BR) were produced in quantity, and treated with the N-Aco-AAF. The treated plasmids were subsequently used for transfecting human fibroblast cells in primary culture.

The analysis of the GFP induced fluorescence shows that numerous cells were transfected.

Applying the selection by antibiotics made it possible to get recombinant clones.

REFERENCES

Cappecchi, 1989, Science, vol. 244:1288
Chen et al., 1987, Mol. Cell. Biol., 7: 2745-2752.
Fraley et al., J.Biol.Chem. 255 (1980) 10431
Flotte et al., 1992, *Am. J Respir. Cell Mol. Biol.,* 7: 349-356.
Fuchs R. P. P. J., 1984, Mol. Biol., 177(1): 173:180.
Feigner et al., 1987, Proc. Natl. Acad. Sci. USA, 84: 7413
Fuller S. A. et al., 1996, *Immunology in Current Protocols in Molecular Biology*, Ausubel et al.
Graham et al., 1973, Virology, 52: 456-457.
Gopal, 1985, Mol. Cell. Biol., 5: 1188-1190.
Harland et al., 1985, J. Cell. Biol., 101: 1094-1095.
Hinds et al., 1999, Microbiology, 154, 519-527.
Kaneda et al., 1989, Science 243: 375
Lefévre et al., 1978, Biochemistry, vol.17: 2561-2567.
Luisi-De-Luca C, 1984, Proc. Natl. Acad. Sci. USA, vol.81: 2831-2835
Maher et al., 1990, Environmental Science Research, 149-156
McLaughlin B A et al., 1996, *Am. J Hum. Genet.,* 59: 561-569.
Nicolau C. et al., 1987, Methods Enzymol., 149:157-76.
Nordeen S K et al., 1988, BioTechniques, 6: 454-457
Pagano et al., 1967, J.Virol. 1:891
Reid et al., 1991, Molecular and Cellular Biology, vol. 11:2769
Samulski et al., 1989, J. Virol., 63: 3822-3828.
Sambrook, J. Fritsch, E. F., and T. Maniatis. 1989. Molecular cloning: a laboratory manual. 2ed. Cold Spring Harbor Laboratory, Cold spring Harbor, N.Y.
Sternberg N. L., 1992, Trends Genet., 8:1-16.
Sternberg N. L., 1994, Mamm. Genome, 5:397-404.
Schmid S E, 1982, Proc. Natl. Acad. Sci. USA, vol.79: 4133 (4137).
Sambrook et Russel, Molecular Cloning, 2001, 3$^{rd}$ edition, CSHL Press.
Schumacher et al., 1998.
Tur-Kaspa et al., 1986, Mol. Cell. Biol., 6:716-718.
Yannisch-Perron C. et al., 1985, Gene, 33: 103-119.

The invention claimed is:

1. A method for in vitro insertion of a nucleic acid of interest initially included in a DNA vector, within a predetermined target nucleotide sequence present in a chromosome contained in a target prokaryotic or eukaryotic cell genome that does not comprise said nucleic acid of interest at said target nucleotide sequence, said method comprising:
   a) providing a DNA vector that comprises the nucleic acid of interest, the DNA vector being replication competent when in said target prokaryotic or eukaryotic cell,
   b) contacting said DNA vector with a mutagenic agent blocking intracellular DNA replication of said DNA vector to produce a modified DNA vector;
   c) transfecting said target prokaryotic or eukaryotic cells with the modified DNA vector obtained at the end of step b) under conditions wherein replication of said modified DNA vector commences and insertion of the nucleic acid of interest within said predetermined target nucleotide sequence occurs; and
   d) selecting prokaryotic or eukaryotic cells for which the nucleic acid of interest has been integrated into the predetermined target nucleotide sequence as a result of said transfecting of step c).

2. The method according to claim 1, further comprising:
   e) selecting from the prokaryotic or eukaryotic cells obtained in step d) the cells wherein the DNA vector sequences, other than those of the nucleic acid of interest, were removed.

3. The method according to claim 1, wherein the mutagenic agent is selected from the group consisting of: N-acetoxy-2-acetylaminofluorene (N-AcO-AAF), an alkylating agent, benzo(a) pyrene-diol-epoxyde (BPDE) and UV irradiation.

4. The method according to claim 2, wherein the mutagenic agent is N-acetoxy-2-acetylaminofluorene (N-AcO-AAF).

5. The method according to claim 4, wherein in step a) the N-AcO-AAF is contacted with the DNA vector comprising the nucleic acid of interest, at a concentration adapted for binding at least 10 N-AcO-AAF molecules per molecule of the polynucleotide.

6. The method according to claim 5, wherein the concentration of N-AcO-AAF is adapted for binding at least 50 N-AcO-AAF molecules per molecule of the polynucleotide.

7. The method according to claim 1, wherein the nucleic acid of interest to be inserted into the chromosome of the prokaryotic or eukaryotic cell, being initially included in said DNA vector, comprises respectively at its 5' terminus and at its 3' terminus sequences having at least 99.5% identity with the corresponding sequences located at the 5' terminus and 3' terminus of the target DNA contained in the chromosome.

8. The method according to claim 7, wherein the sequences respectively located at the 5' terminus and at 3' terminus of the nucleic acid of interest are identical respectively to the 5' terminus and 3' terminus of the target DNA contained in the chromosome.

9. The method according to claim 1, wherein the nucleic acid of interest included in said DNA vector comprises a selection marker nucleotide sequence.

10. The method according to claim 1, wherein the nucleic acid of interest comprises an open reading frame that encodes a protein of therapeutic interest.

11. The method according to claim 1, wherein the nucleic acid of interest comprises an open reading frame disrupted by a heterologous nucleotide sequence.

12. The method according to claim 1, wherein the nucleic acid of interest encodes an antisense RNA.

13. The method according to claim 10, wherein the nucleic acid of interest further comprises a nucleotide sequence with a promoter function, being functional in the selected prokaryotic or eukaryotic host cell, under the control of which the open reading frame or the sequence encoding the RNA included in said nucleic acid of interest is operably arranged.

14. The method according to claim 1, wherein the nucleic acid comprising the nucleic acid of interest comprises a marker nucleotide sequence located, in said polynucleotide, outside the nucleotide sequence of the nucleic acid of interest.

15. The method according to claim 1, wherein said DNA vector is a bacterial plasmid.

16. The method according to claim 1, wherein said DNA vector is a functional plasmid in bacterial cells.

17. The method according to claim 1, wherein said DNA vector is a functional plasmid in human cells.

18. The method according to claim 1, wherein the DNA vector is a double strand linear DNA.

19. The method according to claim 1, wherein the cells transfected in step c) comprise bacterial cells.

20. The method according to claim 1, wherein the cells transfected in step c) consist of non human mammalian cells.

21. The method according to claim 1, wherein the cells transfected in step c) consist of human cells.

22. A method for targeted insertion of a nucleic acid of interest into a selected location of the genome of a target cell, the method comprising:

a) providing a DNA vector comprising the nucleic acid of interest, the DNA vector capable of replicating in the target cell;
b) contacting the DNA vector in vitro with a mutagenic agent that blocks replication of the DNA vector to produce a modified DNA vector;
c) transfecting a population of target cells with the modified DNA vector;
d) maintaining the transfected target cells under conditions in which the modified DNA vector can replicate in the target cell and integrate into the genome of the target cell; and
e) selecting cells in which the nucleic acid of interest has been integrated into the selected location of the genome of the target cell.

23. The method according to claim 22, wherein the mutagenic agent is a natural or synthetic chemical compound that binds to nucleic acid.

24. The method according to claim 22, wherein the DNA vector comprises at least one functional replication origin for the target cell.

\* \* \* \* \*

UNITED STATES PATENT AND TRADEMARK OFFICE
CERTIFICATE OF CORRECTION

PATENT NO. : 8,609,419 B2
APPLICATION NO. : 10/532663
DATED : December 17, 2013
INVENTOR(S) : Fuchs et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1613 days.

Signed and Sealed this

Twenty-second Day of September, 2015

Michelle K. Lee
*Director of the United States Patent and Trademark Office*